US009775724B2

United States Patent
Blaylock et al.

(10) Patent No.: US 9,775,724 B2
(45) Date of Patent: Oct. 3, 2017

(54) PROSTHETIC INSERTER

(71) Applicant: Zimmer, Inc., Warsaw, IN (US)

(72) Inventors: Jeff Blaylock, Fort Wayne, IN (US);
Jody L. Claypool, Warsaw, IN (US);
Stephen H. Hoag, Warsaw, IN (US);
Anthony Romano, Columbia City, IN (US)

(73) Assignee: Zimmer, Inc., Warsaw, IN (US)

( * ) Notice: Subject to any disclaimer, the term of this patent is extended or adjusted under 35 U.S.C. 154(b) by 84 days.

(21) Appl. No.: 14/712,415

(22) Filed: May 14, 2015

(65) Prior Publication Data
US 2015/0250613 A1    Sep. 10, 2015

Related U.S. Application Data

(63) Continuation of application No. 12/961,916, filed on Dec. 7, 2010, now Pat. No. 9,039,710.

(51) Int. Cl.
*A61F 2/46* (2006.01)
*A61B 17/92* (2006.01)
(Continued)

(52) U.S. Cl.
CPC .............. *A61F 2/461* (2013.01); *A61B 17/92* (2013.01); *A61F 2/3859* (2013.01);
(Continued)

(58) Field of Classification Search
CPC . A61F 2/4603; A61F 2/46; A61D 2002/4624; A61B 17/92
(Continued)

(56) References Cited

U.S. PATENT DOCUMENTS

| 994,804 | A | * | 6/1911 | Wahlstrom | A47G 21/18 |
| | | | | | 125/36 |
| 1,756,003 | A | * | 4/1930 | North | B25B 23/065 |
| | | | | | 81/114 |

(Continued)

FOREIGN PATENT DOCUMENTS

EP    2588038 A1    5/2013

OTHER PUBLICATIONS

"European Application Serial No. 11796894.1, Decision to grant dated Jan. 28, 2016", 2 pgs.
(Continued)

*Primary Examiner* — Christian Sevilla
(74) *Attorney, Agent, or Firm* — Schwegman Lundberg & Woessner, P.A.

(57) ABSTRACT

A prosthetic inserter includes an inserter head having at least first and second bosses, at least one of the bosses movable from a first position to a second position, that couple the inserter to a femoral provisional component via a pair of corresponding apertures, such as drill holes, within the articulating surfaces of a selected one of a series of femoral provisional components. Each provisional component of the series is capable of having different aperture distances measured between a respective pair of apertures. The bosses of the inserter are biased into an engagement position in which the inserter can be secured to a femoral provisional component to eliminate the need for an external engagement force to be supplied to the inserter.

20 Claims, 12 Drawing Sheets

(51) Int. Cl.
   *A61F 2/38* (2006.01)
   *A61F 2/30* (2006.01)
(52) U.S. Cl.
   CPC ...... *A61F 2/4684* (2013.01); *A61B 2017/922* (2013.01); *A61F 2002/3037* (2013.01); *A61F 2002/30354* (2013.01); *A61F 2002/30505* (2013.01); *A61F 2002/4624* (2013.01); *A61F 2002/4628* (2013.01); *A61F 2002/4681* (2013.01)
(58) Field of Classification Search
   USPC .................................................. 81/177.85
   See application file for complete search history.

(56) References Cited

U.S. PATENT DOCUMENTS

| | | | | |
|---|---|---|---|---|
| 2,162,359 A * | 6/1939 | Rhinevault | ......... | B25B 23/0035 279/81 |
| 2,474,360 A * | 6/1949 | Jimerson | ............. | B25B 23/0035 279/76 |
| 2,501,386 A * | 3/1950 | Gibbs | ................. | B25B 21/007 192/34 |
| 2,549,397 A * | 4/1951 | Sparks | ............... | B25B 23/0035 403/328 |
| 2,712,765 A * | 7/1955 | Knight, Jr. | ............. | B25G 1/007 81/177.1 |
| 2,968,205 A | 1/1961 | Springate | | |
| 2,987,334 A * | 6/1961 | Wendling | ............ | B25B 23/0014 279/76 |
| 3,170,362 A * | 2/1965 | Mewse | ................. | F16B 21/165 24/453 |
| 3,378,905 A * | 4/1968 | Szohatzky | ........... | B21D 39/046 279/76 |
| 3,802,302 A | 4/1974 | Bengtson | | |
| 4,245,528 A * | 1/1981 | Hugh | ................. | B25B 23/0035 81/177.85 |
| 4,317,392 A * | 3/1982 | Stephens | ............ | B25B 23/0035 81/177.85 |
| 4,480,497 A | 11/1984 | Locher | | |
| 4,537,100 A * | 8/1985 | Palm | ................... | B25B 23/0035 403/325 |
| 4,817,476 A * | 4/1989 | Karge | ................. | B25B 23/0035 81/177.2 |
| 4,865,485 A * | 9/1989 | Finnefrock, Sr. | ... | B25B 23/0021 403/17 |
| 4,962,682 A * | 10/1990 | Rose | ................... | B25B 23/0021 81/177.1 |
| 4,988,248 A * | 1/1991 | Flux | ........................ | F16B 21/16 280/507 |
| 5,059,196 A | 10/1991 | Coates | | |
| 5,090,278 A | 2/1992 | Mair et al. | | |
| 5,098,437 A | 3/1992 | Kashuba et al. | | |
| 5,169,399 A | 12/1992 | Ryland et al. | | |
| 5,171,243 A | 12/1992 | Kashuba et al. | | |
| 5,309,798 A | 5/1994 | Markwart et al. | | |
| 5,386,747 A * | 2/1995 | Grover | ............... | B25B 23/0035 81/177.85 |
| 5,394,594 A * | 3/1995 | Duran | ................. | F16B 21/165 16/422 |
| 5,417,693 A | 5/1995 | Sowden et al. | | |
| 5,417,696 A | 5/1995 | Kashuba et al. | | |
| 5,450,773 A * | 9/1995 | Darrah | ................. | B25B 21/004 81/57.39 |
| 5,683,399 A | 11/1997 | Jones | | |
| 5,720,207 A * | 2/1998 | Milner | ................. | B25B 23/0035 81/177.2 |
| 5,732,992 A | 3/1998 | Mauldin | | |
| 5,928,287 A | 7/1999 | Keller | | |
| 5,954,463 A | 9/1999 | Jore | | |
| 6,003,414 A * | 12/1999 | Hsieh | ................. | B25B 23/0014 403/325 |
| 6,006,631 A * | 12/1999 | Miner | ................. | B25B 23/0035 81/177.85 |
| 6,006,632 A * | 12/1999 | Hsieh | ................. | B25B 23/0021 403/322.1 |
| 6,033,405 A * | 3/2000 | Winslow | .............. | A61B 17/861 606/86 R |
| 6,067,881 A * | 5/2000 | Albertson | ........... | B25B 23/0035 192/44 |
| 6,327,941 B1 * | 12/2001 | Cheng | ................. | B25B 23/0021 81/177.1 |
| 6,386,789 B1 * | 5/2002 | Chausse | ................ | F16B 21/165 403/322.2 |
| 6,823,762 B2 * | 11/2004 | Hu | ...................... | B25B 23/0035 403/322.2 |
| 6,874,392 B1 * | 4/2005 | Wu | ..................... | B25B 23/0035 81/177.2 |
| 6,916,324 B2 | 7/2005 | Sanford et al. | | |
| 7,048,742 B2 | 5/2006 | Keller | | |
| 7,338,497 B2 | 3/2008 | Coon et al. | | |
| 7,441,482 B2 * | 10/2008 | Lin | ....................... | B25B 13/463 81/177.85 |
| 7,895,924 B2 * | 3/2011 | Hsieh | ................... | B25B 15/001 81/177.85 |
| 8,474,353 B1 * | 7/2013 | Thoman | ................ | B25G 1/007 81/177.6 |
| 9,039,710 B2 | 5/2015 | Blaylock et al. | | |
| 2002/0162426 A1 * | 11/2002 | Lee | ..................... | B25B 23/0035 81/177.85 |
| 2002/0189409 A1 * | 12/2002 | Lee | ..................... | B25B 23/0021 81/177.85 |
| 2004/0010261 A1 | 1/2004 | Hoag et al. | | |
| 2006/0200162 A1 | 9/2006 | Farling et al. | | |
| 2006/0230885 A1 * | 10/2006 | Olson | ..................... | B25B 23/16 81/177.85 |
| 2007/0043442 A1 | 2/2007 | Abernathie et al. | | |
| 2007/0163406 A1 * | 7/2007 | Liu | ........................ | B25G 1/005 81/177.85 |
| 2007/0173858 A1 | 7/2007 | Engh et al. | | |
| 2008/0087143 A1 * | 4/2008 | Hsieh | ...................... | B25G 3/18 81/177.85 |
| 2008/0154382 A1 | 6/2008 | De Villiers et al. | | |
| 2009/0036909 A1 | 2/2009 | Perry et al. | | |
| 2010/0082074 A1 | 4/2010 | Long et al. | | |
| 2012/0143204 A1 * | 6/2012 | Blaylock | ............... | A61F 2/3859 606/99 |

OTHER PUBLICATIONS

"European Application Serial No. 11796894.1, Intention to grant dated Jun. 17, 2015", 42 pgs.
"European Application Serial No. 11796894.1, Response filed Nov. 13, 2014 to Examination Notification Art. 94(3) dated Jul. 3, 2014", 18 pgs.
"International Application Serial No. PCT/US2011/063260, International Preliminary Report on Patentability dated Jun. 20, 2013", 8 pgs.
"U.S. Appl. No. 12/961,916, Advisory Action dated Sep. 27, 2013", 3 pgs.
"U.S. Appl. No. 12/961,916, Final Office Action dated Jul. 17, 2013", 11 pgs.
"U.S. Appl. No. 12/961,916, Non Final Office Action dated Feb. 13, 2013", 9 pgs.
"U.S. Appl. No. 12/961,916, Non Final Office Action dated Aug. 20, 2014", 9 pgs.
"U.S. Appl. No. 12/961,916, Notice of Allowance dated Jan. 22, 2015", 7 pgs.
"U.S. Appl. No. 12/961,916, PTO Response to Rule 312 Communication dated Apr. 30, 2015", 2 pgs.
"U.S. Appl. No. 12/961,916, Response filed Jan. 29, 2013 to Restriction Requirement dated Jan. 15, 2013", 10 pgs.
"U.S. Appl. No. 12/961,916, Response filed May 13, 2013 to Non Final Office Action dated Feb. 13, 2013", 10 pgs.
"U.S. Appl. No. 12/961,916, Response filed Sep. 17, 2013 to Final Office Action dated Jul. 17, 2013", 10 pgs.
"U.S. Appl. No. 12/961,916, Response filed Nov. 20, 2014 to Non Final Office Action dated Aug. 20, 2014", 13 pgs.

(56) References Cited

OTHER PUBLICATIONS

"U.S. Appl. No. 12/961,916, Response filed Dec. 17, 2012 to Restriction Requirement mailed Oct. 19, 2012", 13 pgs.
"U.S. Appl. No. 12/961,916, Restriction Requirement dated Jan. 15, 2013", 8 pgs.
"U.S. Appl. No. 12/961,916, Restriction Requirement dated Oct. 19, 2012", 6 pgs.
"European Application Serial No. 11796894.1, Examination Notification Art. 94(3) dated Jul. 3, 2014", 5 pgs.
"International Application Serial No. PCT/US2011/063260, International Search Report and Written Opinion Dated Feb. 3, 2012", 13 pgs.
"Triathlon Knee System Surgical Protocol", Draft Surgical Protocol, Stryker, (2006), 40-41.
"Zimmer NexGen CR-Flex and LPS-Flex Knees Surgical Technique with posterior Referencing Instrumentation.", Zimmer Inc., (2010, 2011), 48 pgs.

\* cited by examiner

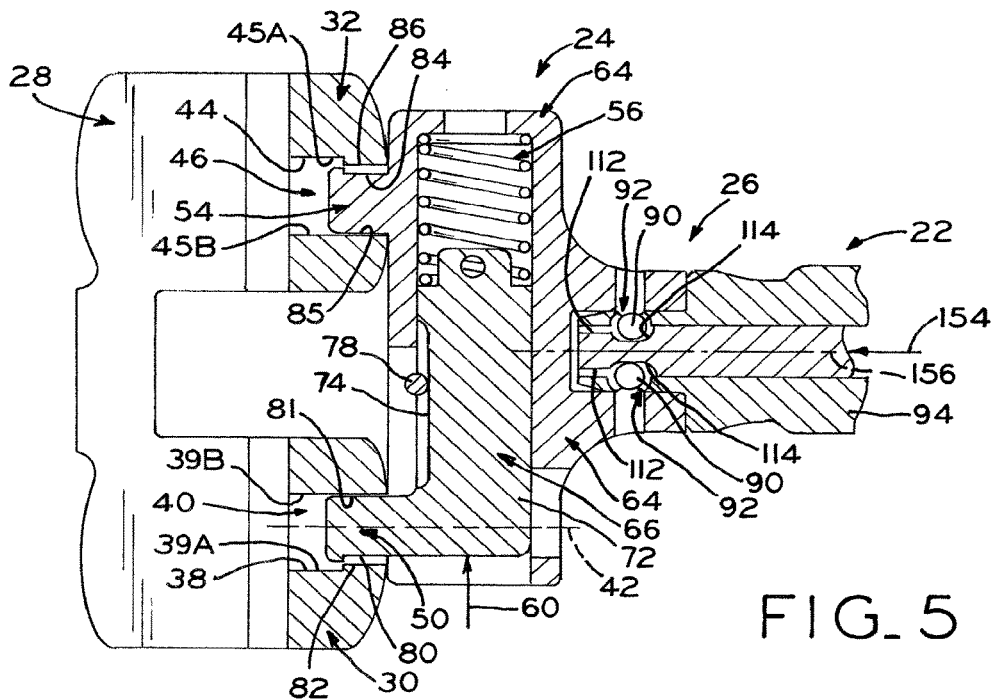
FIG_5
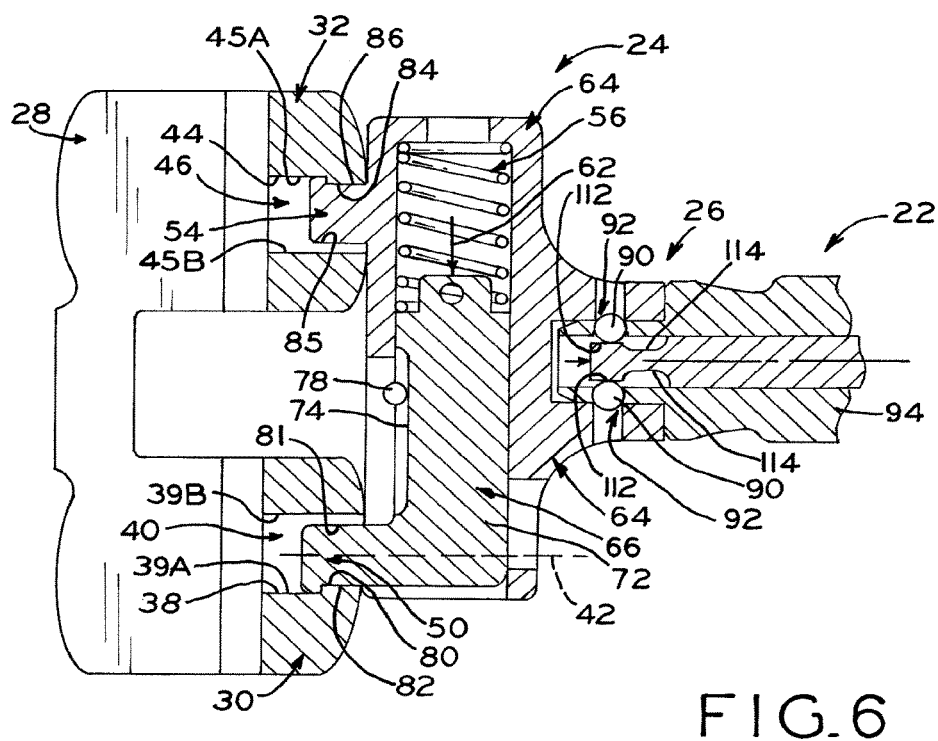
FIG_6

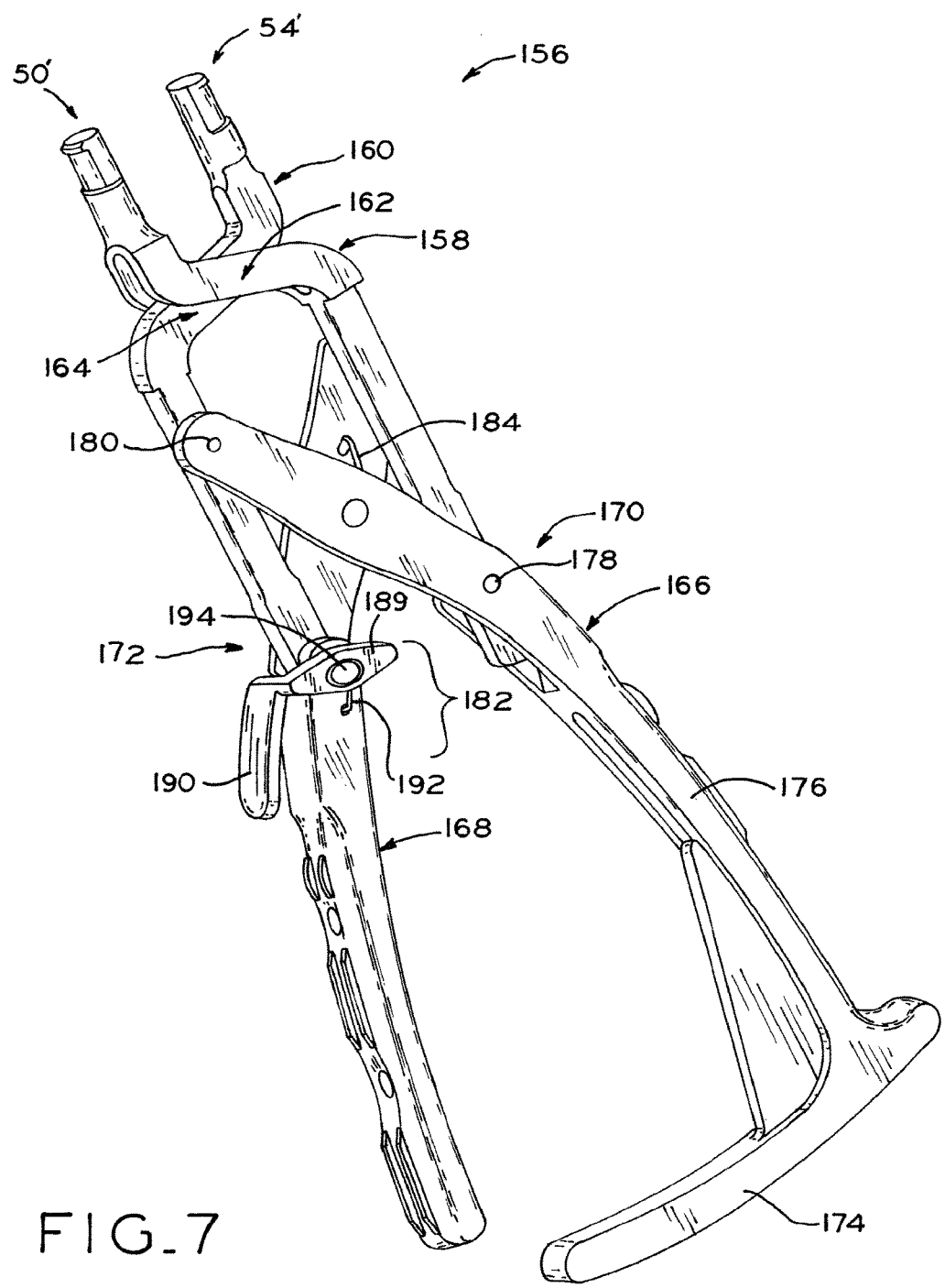
FIG_7

PROSTHETIC INSERTER

CROSS-REFERENCE TO RELATED APPLICATIONS

The present application is a continuation of U.S. patent application Ser. No. 12/961,916, filed on Dec. 7, 2010, now issued as U.S. Pat. No. 9,039,710, the disclosure, drawings, and claims of which are expressly incorporated by reference herein in their entirety.

BACKGROUND

1. Field of Invention

The present invention relates to instruments used in orthopedic surgery, and, in particular, to a prosthetic inserter, such as an impactor-extractor for use with the impaction and extraction of a femoral provisional component, for example.

2. Description of Related Art

The knee is the joint between the femur and the tibia. The knee joint is formed of a pair of condyles located at a distal portion of the femur, a tibial plateau located at a proximal end of the tibia and shaped to mate with the pair of condyles, and a pair of menisci positioned between the tibial plateau and the condyles. A knee may incur a significant disease or trauma that warrants replacement of the knee with a prosthetic knee implant including prosthetic components such as a femoral component to replace the distal end of the femur, a tibial component to replace the proximal end of the tibia, and a bearing insert to replace articulating tissue between the femur and the tibia.

Orthopedic procedures for the replacement of all, or a portion of, a patient's joint typically require resecting (cutting) and reshaping of the bones of the knee joint to receive such prosthetic components. Procedures for implanting a total knee prosthesis typically involve preparing and reshaping both the distal end of the femur and the proximal end of the tibia prior to implanting the respective prosthetic components. Resection of the femur generally involves making five intersecting generally planar cuts, and resection of the tibial plateau generally involves only a single cut. The amount of bone removed is determined, in part, by the size and type of components being implanted.

During a surgical procedure to implant a prosthetic knee joint, a provisional femoral component and a provisional tibial component can be placed on a distal femur and proximal tibia, respectively, after resecting the distal femur and proximal tibia. The provisional components assist with confirming the proper size and position of the permanent femoral and tibial components. The provisional components typically come in a range of sizes that are identical in size and shape to the permanent components and are typically selected after making a preliminary determination of the proper size of the permanent components. A trial reduction of the knee joint with the provisional components in place may indicate that the preliminary size determination was incorrect, that the gap between the femur and tibia is insufficient, or that some other undesirable characteristic requires the selection of a differently sized tibial or femoral component.

Minimally invasive knee surgeries are becoming increasingly popular and employ, among other things, considerably smaller incisions. Such small incisions lead to tighter working spaces, but promote reduced trauma to nearby tissue and, thereby, accelerate post-operative recovery. Proper insertion and extraction of the provisional components requires reliable grasping and manipulation of the provisional components in a small space.

SUMMARY

The present disclosure provides a prosthetic inserter that includes an inserter head having at least first and second bosses that couple the inserter to a femoral provisional component via a pair of corresponding apertures, such as drill holes, within the articulating surfaces of a selected one of a series of femoral provisional components. Each provisional component of the series is capable of having different aperture distances measured between a respective pair of apertures. For example, while the first and second bosses are able to couple to a first selected femoral provisional component having a first aperture distance, at least one of the bosses is movable from a first position to a second position to allow engagement with a pair of apertures in a second selected femoral provisional component having a second aperture distance. The bosses of the inserter are biased into an engagement position in which the inserter can be secured to a femoral provisional component to eliminate the need for an external engagement force to be supplied to the inserter.

In one form thereof, the present disclosure provides a combination, including a femoral provisional component femoral provisional component having a medial condyle and a lateral condyle, the medial condyle having a medial condyle wall forming a medial condyle aperture having a medial condyle aperture longitudinal axis, the lateral condyle having a lateral condyle wall forming a lateral condyle aperture, the medial condyle aperture spaced an aperture distance from the lateral condyle aperture; and a femoral provisional inserter connectable with the femoral provisional component, the femoral provisional inserter including an inserter head including a medial boss having a medial boss longitudinal axis, the medial boss sized for receipt within the medial condyle aperture, a lateral boss, said lateral boss sized for receipt within the lateral condyle aperture, at least one of the medial boss and the lateral boss defining a movable boss movable relative to the other of the medial boss and the lateral boss along a direction transverse to the medial boss longitudinal axis, and a biasing member biasing the movable boss into an at rest position, the movable boss movable from the at rest position into an actuated position via an actuating force acting against a biasing force of the biasing member, the medial boss spaced a boss distance from the lateral boss; wherein movement of the movable boss to the actuated position is capable of changing the boss distance to be equal to said aperture distance. With the movable boss maintaining the actuated position, the medial boss can be inserted into the medial condyle aperture and the lateral boss can be inserted into the lateral condyle aperture, and with the medial boss and the lateral boss respectively inserted into the medial aperture and the lateral aperture, the actuating force can be removed so that the biasing force biases the medial boss and the lateral boss into frictional engagement with a respective one of the medial condyle wall and the lateral condyle wall in the femoral provisional component.

In another form thereof, the present disclosure provides a femoral provisional system, a first femoral provisional component having a first medial condyle and a first lateral condyle, the first medial condyle having a first medial condyle wall forming a first medial condyle aperture having a first medial condyle aperture longitudinal axis, the first lateral condyle having a first lateral condyle wall forming a first lateral condyle aperture, the first medial condyle aperture spaced a first aperture distance from the first lateral condyle aperture; a second femoral provisional component having a second medial condyle and a second lateral condyle, the second medial condyle having a second medial condyle wall forming a second medial condyle aperture having a second medial condyle aperture longitudinal axis, the second lateral condyle having a second lateral condyle wall forming a second lateral condyle aperture, the second medial condyle aperture spaced a second aperture distance from the second lateral condyle aperture, wherein the first aperture distance does not equal the second aperture distance; and a femoral provisional inserter including an inserter head including a medial boss having a medial boss longitudinal axis, the medial boss sized for receipt alternatively within the first and the second medial condyle apertures, a lateral boss, the lateral boss sized for receipt alternatively within the first and the second lateral condyle apertures, at least one of the medial boss and the lateral boss defining a movable boss movable relative to the other of the medial boss and the lateral boss along a direction transverse to the medial boss longitudinal axis, and a biasing member biasing the movable boss into an at rest position, the movable boss movable from the at rest position into an actuated position via an actuating force acting against a biasing force of the biasing member, the medial boss spaced a boss distance from the lateral boss; wherein movement of the movable boss to the actuated position is capable of changing the boss distance to be equal to at least one of the first aperture distance and the second aperture distance. With the movable boss maintaining the actuated position and the boss distance changed to be equal to one of the first aperture distance and the second aperture distance, the medial boss can be inserted into a respective one of the first medial condyle aperture and the second medial condyle aperture and the lateral boss can be inserted into a respective one of the first lateral condyle aperture and the second lateral condyle aperture, and with the medial boss inserted into a respective one of the first medial aperture and the second medial aperture and the lateral boss inserted into a respective one of the first lateral aperture and the second lateral aperture, the actuating force can be removed so that the biasing force biases the medial boss and the lateral boss into frictional engagement with, respectively, a respective one of the first and second medial condyle walls and a respective one of the first and second lateral condyle walls in a respective one of the first and second femoral provisional components.

In yet another form thereof, the present disclosure provides a method of connecting a femoral provisional component and a femoral provisional inserter, the method including the steps of providing the femoral provisional component comprising a medial condyle and a lateral condyle, the medial condyle having a medial condyle wall forming a medial condyle aperture having a medial condyle aperture longitudinal axis, the lateral condyle having a lateral condyle wall forming a lateral condyle aperture, the medial condyle aperture spaced an aperture distance from the lateral condyle aperture; and providing the femoral provisional inserter including an inserter head including a medial boss having a medial boss longitudinal axis, the medial boss sized for receipt within the medial condyle aperture, a lateral boss, the lateral boss sized for receipt within the lateral condyle aperture, at least one of the medial boss and the lateral boss defining a movable boss movable relative to the other of the medial boss and the lateral boss along a direction transverse to the medial boss longitudinal axis, the medial boss spaced a boss distance from the lateral boss, and a biasing member biasing the movable boss into an at rest position, applying an actuating force to move the movable boss from the at rest position into an actuated position in which the boss distance is equal to the aperture distance, the actuating force acting against a biasing force of the biasing member, while maintaining the actuated position of the movable boss, inserting the medial boss into the medial condyle aperture and the lateral boss into the lateral condyle aperture, and after inserting the medial boss into the medial condyle aperture and the lateral boss into the lateral condyle aperture, removing the actuating force so that the biasing force biases the medial boss and the lateral boss into frictional engagement with a respective one of the medial condyle wall and the lateral condyle wall in the femoral provisional component.

BRIEF DESCRIPTION OF THE DRAWINGS

The above-mentioned and other features and advantages of this disclosure, and the manner of attaining them, will become more apparent and the invention itself will be better understood by reference to the following descriptions of embodiments of the invention taken in conjunction with the accompanying drawings, wherein:

FIG. 5 is a cross sectional view taken along line A-A of FIG. 4 illustrating the inserter head illustrated in FIG. 1 actuated to allow bosses 50, 54 to enter or exit apertures 40, 46 of the femoral provisional component of FIG. 1;

FIG. 6 is a cross-sectional view taken along line A-A of FIG. 4 illustrating the inserter head illustrated in FIG. 1 with bosses 50, 54 biased into engagement with the femoral provisional component illustrated in FIG. 1;

FIG. 7 is a perspective view of another embodiment of an inserter according to the present invention;

Corresponding reference characters indicate corresponding parts throughout the several views. The exemplifications set out herein illustrate exemplary embodiments of the invention, and such exemplifications are not to be construed as limiting the scope of the disclosure in any manner.

DETAILED DESCRIPTION

A prosthetic inserter includes an inserter head having at least a medial boss and a lateral boss that couple the inserter to a femoral provisional component via a pair of corresponding apertures, such as drill holes, within the articulating surfaces, or a respective medial condyle and a lateral condyle, of a selected one of a series of femoral provisional components. The medial boss and the lateral boss are able to couple to a first selected femoral provisional component defining a first aperture distance between a first pair of corresponding apertures. As at least one of the bosses is movable from a first, at rest position to a second, actuated position, the medial boss and the lateral boss may further engage the inserter to a femoral provisional component via a second pair of apertures defining a second aperture distance in a second selected femoral provisional component.

Moreover, a handle is connected to the inserter head and includes a single bar body or a multi-bar body, as described further below, such that the connection of the handle to the inserter head allows for the application of a centralized force upon the provisional component to prevent, for example, tilting of the provisional component during implantation. Further, the profile of the inserter head and handle connection allows the inserter to remain substantially within the outer periphery, or "envelope", of the provisional component or to only slightly extend beyond the outer periphery and does not require the expansion of the surgical field, or incision to the body, beyond that required by the outer periphery of the provisional component.

Figure 1:
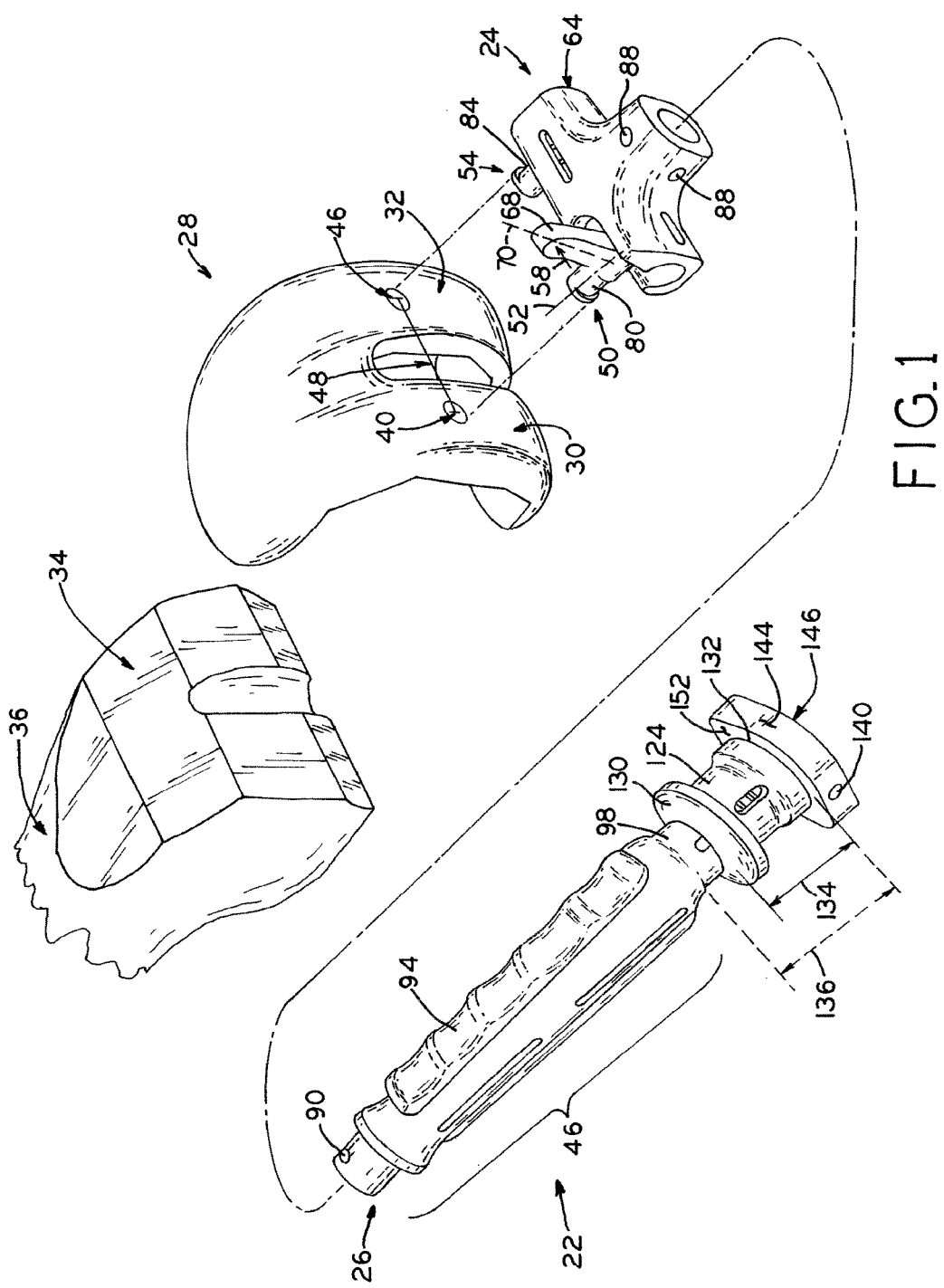
FIG. 1 is an exploded perspective view of an inserter assembly according to the present invention including an inserter head, a handle, an exemplary femoral provisional component, and a resected femoral bone.
Figure 4:
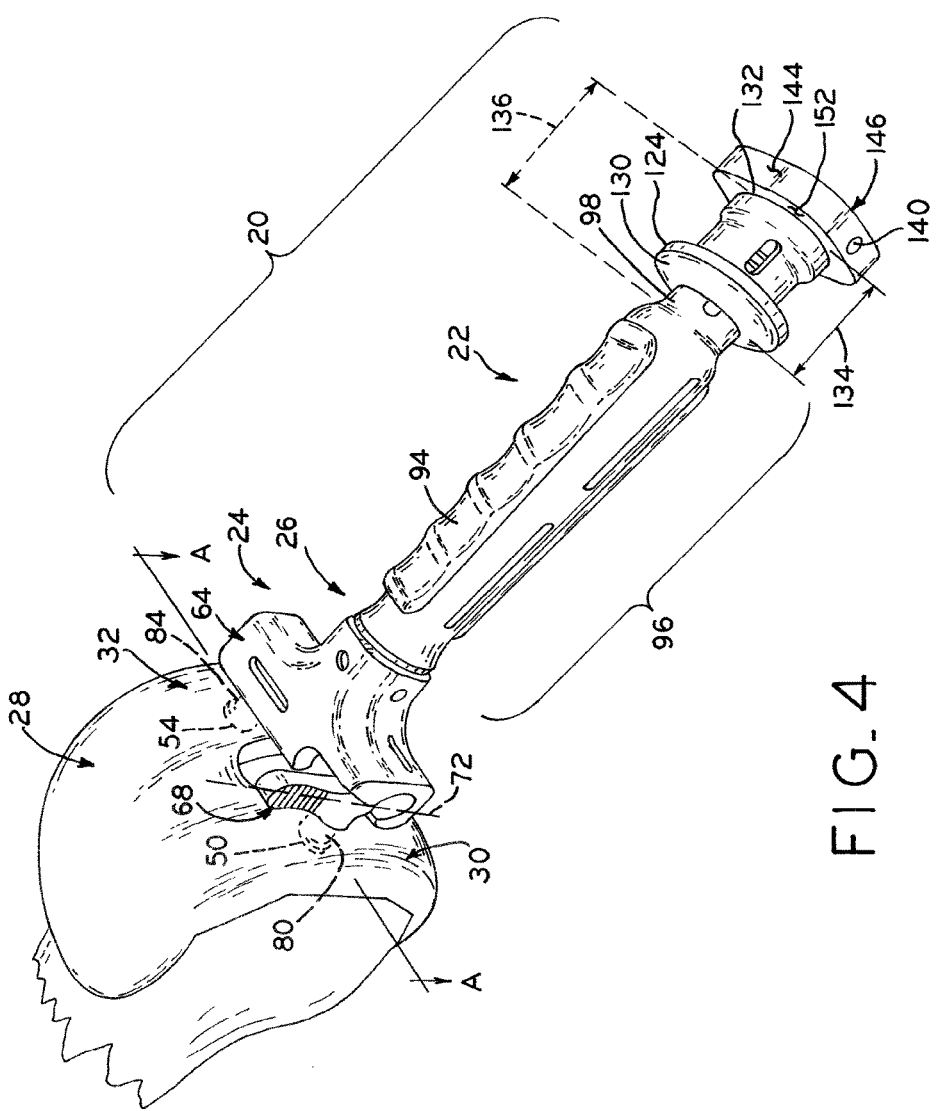
FIG. 4 is a perspective view of the inserter assembly of FIG. 1 showing the inserter secured to the femoral provisional component of FIG. 1.

For example, referring to FIGS. 1 and 4, femoral provisional inserter 20 (FIG. 4) includes handle 22 and inserter head 24. Handle 22 (FIG. 1), discussed further below, is removably connectable at proximal end 26 to inserter head 24, and femoral provisional inserter 20 is connectable via inserter head 24 to femoral provisional component 28. Further, femoral provisional component 28 includes medial condyle 30 and lateral condyle 32 and is capable of being positioned on prepared resection area 34 of femur 36. The "envelope" of femoral provisional component 28 includes a medial to lateral extent and an anterior to posterior extent that together define an outer periphery of femoral provisional component 28. The medial to lateral extent of femoral provisional component 28 is wider in dimension than the medial to lateral extents of both inserter head 24 and handle 22. Similarly, the anterior to posterior extent of femoral provisional component 28 is wider in dimension than the anterior to posterior extents of both inserter head 24 and handle 22. As the medial to lateral and anterior to posterior extents of inserter head 24 and handle 22, together defining femoral provisional inserter 20, are smaller in dimension than the respective extents of femoral provisional component 28, femoral provisional inserter 20 remains substantially within the outer periphery, or "envelope", of femoral provisional component 28 and does not require the expansion of the surgical field beyond that required by the outer periphery of femoral provisional component 28.

Referring to FIGS. 5 and 6, medial condyle 30 includes medial condyle wall 38 forming medial condyle aperture 40 having medial condyle aperture longitudinal axis 42. Medial condyle wall 38 includes medial-most wall surface 39A and lateral-most wall surface 39B. Lateral condyle 32 includes lateral condyle wall 44 forming lateral condyle aperture 46. Lateral condyle wall 44 includes lateral-most wall surface 45A and medial-most wall surface 45B. Referring back to FIG. 1, medial condyle aperture 40 is spaced aperture distance 48 from lateral condyle aperture 46. Spaced aperture distance 48 is measured between points defining centers of apertures 40 and 46. Femoral provisional component 28 may be a first femoral provisional component of a series including, for example, a second femoral provisional component 28' (FIG. 14) similar to the first femoral provisional component 28 with the exception that the second femoral provisional component 28' includes a second aperture distance 48' defined between second medial condyle aperture 40' and second lateral condyle aperture 46' such that second aperture distance 48' of second femoral provisional component 28' is different from the spaced aperture distance 48 of the first femoral provisional component 28. Second provisional component 28' may represent a femoral prosthesis of a different size relative to the femoral prosthesis represented by femoral provisional component 28.

Referring back to FIG. 1, inserter head 24 of femoral provisional inserter 20 includes medial boss 50 having medial boss longitudinal axis 52. Medial boss 50 is sized for receipt within medial condyle aperture 40 (FIG. 1). Inserter head 24 also includes lateral boss 54. Lateral boss 54 is sized for receipt within lateral condyle aperture 46. At least one of medial boss 50 and lateral boss 54, define a movable boss movable relative to the other of medial boss 50 and lateral boss 54 along a direction transverse to medial boss longitudinal axis 52 and medial condyle aperture longitudinal axis 42 (FIGS. 5 and 6).

Medial boss 50 is spaced a movable boss distance from lateral boss 54, a boss distance measurable between points defining centers of bosses 50 and 54. Medial boss 50 is initially spaced at rest a maximum distance away from lateral boss 54 by biasing member 56 of inserter head 24. The movable boss is movable from the at rest position, described further below as occurring via a physical stop within inserter head 24, along the direction of arrow 58 (FIG. 1) into an actuated position via actuating force 60 (FIG. 5) acting against biasing force 62 (FIG. 6) of biasing member 56.

Figure 3:
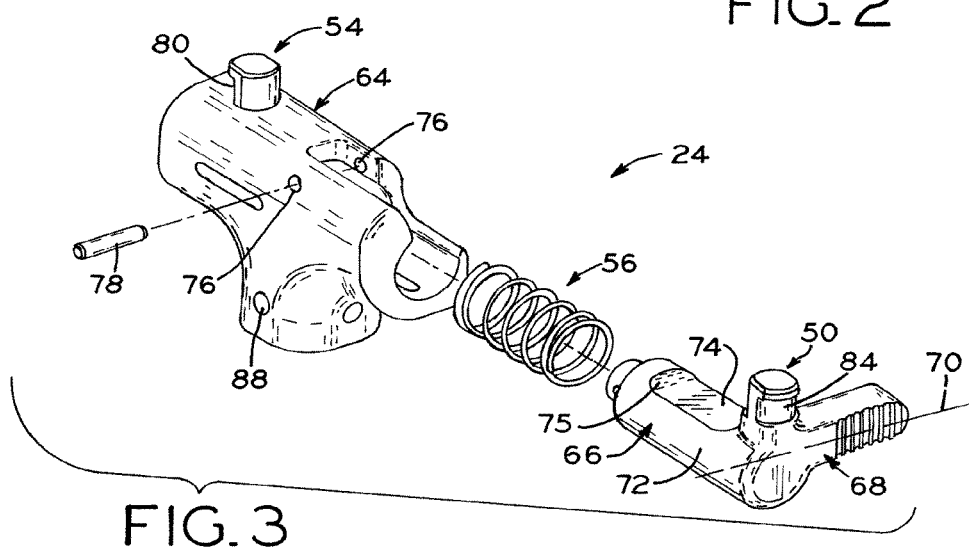
FIG. 3 is an exploded perspective view of an embodiment of the inserter head of FIG. 1.

Referring to FIG. 3, inserter head 24 includes stationary body 64 and piston body 66. Biasing member 56 is housed in stationary body 64, and stationary body 64 receives piston body 66, which is movable within stationary body 64. Lateral boss 54 is connected to stationary body 64, and medial boss 50 is connected to piston body 66. In an alternate embodiment, lateral boss 54 could be connected to piston body 66 and medial boss 50 could be connected to stationary body 64. Piston body 66 includes protrusion 68 having protrusion longitudinal axis 70. Protrusion 68 extends radially from piston body 66 such that protrusion longitudinal axis 70 is transverse to a longitudinal axis of piston body 66.

In an exemplary embodiment, biasing member 56 is a spring, and piston body 66 includes piston 72, having a generally cylindrical cross-section. Biasing member 56 abuts piston 72. Force applied to protrusion 68 transverse to protrusion longitudinal axis 70 generates actuating force 60 (FIG. 5) which acts against the biasing force of biasing member 56 disposed within stationary body 64.

As shown in FIGS. 3, 5, and 6, piston 72 includes flat 74. Stationary body 64 includes a pair of parallel holes 76 disposed proximal to flat 74 of piston body 66 after piston body 66 is received into stationary body 64. Parallel holes 76 receive pin 78, which rests against flat 74 as shown in FIGS. 5 and 6. After receipt through holes 76 and in an at rest position of piston body 66, pin 78 abuts pin stop surface 75, which proximally projects from flat 74, so that the abutment of pin 78 with pin stop surface 75 acts as a physical stop to movement of piston body 66 within stationary body 64 in a direction along arrow 58 (FIG. 1). Flat 74 and pin 78 together act to key piston 72 to stationary body 64 to prevent rotation of piston 72 within stationary body 64 and to set medial boss 50 into parallel alignment with lateral boss 54. In an alternate embodiment, piston body 66 has a non-circular cross-section received in a longitudinal aperture of stationary body 64 of similar cross-section to key piston body 66 to stationary body 64.

When the movable boss is in the at rest position, the boss distance may not be equal to the aperture distance of the selected femoral provisional component, for example, femoral provisional component 28. Movement of the movable boss to the actuated position is capable of changing the boss distance to be equal to the aperture distance. With the movable boss maintaining the actuated position, medial boss 50 can be inserted into medial condyle aperture 40 and lateral boss 54 can be inserted into lateral condyle aperture 46. After such an insertion, as described further below, actuating force 60 can be removed so that biasing force 62 biases medial boss 50 into frictional engagement with medial condyle wall 38 and lateral boss 54 into frictional engagement with lateral condyle wall 44 in femoral provisional component 28, for example. In the embodiment described above, the biasing occurs in an outwards direction such that medial boss 50 moves away from lateral boss 54. Alternatively, the biasing force may bias medial boss 50 to move towards lateral boss 54. A similar biasing occurs with use of another selected femoral provisional component, such as, for example, second femoral provisional component 28'.

Such frictional engagement occurs via medial boss 50 of femoral provisional component 28 matingly engaging medial condyle wall 38 and lateral boss 54 matingly engaging lateral condyle wall 44. Illustrating a medial mating shoulder arrangement forming a physical stop or barrier to resist withdrawal of medial boss 50 from medial condyle wall 38, medial boss 50 of FIGS. 5 and 6 includes medial notch 80 and medial condyle wall 38 includes medial protrusion 82 on medial-most wall surface 39A. Further illustrating a lateral mating shoulder arrangement to resist withdrawal of lateral boss 54 from lateral condyle wall 44, lateral boss 54 of FIGS. 5 and 6 includes lateral notch 84 and lateral condyle wall 44 includes lateral protrusion 86 on lateral-most wall surface 45A. Alternatively, the medial mating shoulder arrangement may include medial boss 50 having a medial protrusion and medial condyle wall 38 including a medial notch, and the lateral mating shoulder arrangement may include lateral boss 54 having a lateral protrusion and lateral condyle wall 44 including a lateral notch.

Continuing to refer to FIGS. 5 and 6, after medial boss 50 and lateral boss 54 have been respectively inserted into medial condyle aperture 40 and lateral condyle aperture 46 (FIG. 5), actuating force 60 can be removed so that biasing force 62 (FIG. 6) biases medial boss 50 and lateral boss 54 into frictional engagement with a respective one of medial condyle wall 38 and lateral condyle wall 44. The respective mating shoulder arrangements (FIG. 6) form a physical stop perpendicular to the direction of withdrawal to resist withdrawal of bosses 50, 54 from walls 38, 44, respectively. The medial mating shoulder arrangement and the lateral mating shoulder arrangement allow for a cooperating engagement between a respective one of medial boss 50 and lateral boss 54 with a respective one of medial condyle wall 38 and lateral condyle wall 44. Together, the cooperating engagement and frictional engagement of the engaged bosses resist withdrawal of inserter 20 from femoral provisional component 28 as the engaged bosses are prevented from displacement from the respective apertures into which they are inserted and with which they are engaged.

As described above, the moveable boss moves from the at rest position to a position in which medial boss 50 can be inserted into medial condyle aperture 40 and lateral boss 54 can be inserted into lateral condyle aperture 46. Referring to FIG. 5, in this insertable, actuated position, end 81 of medial boss 50, opposite an end including medial notch 80, is positioned to substantially abut and be slidably received along lateral-most wall surface 39B of medial condyle wall 38, and end 85 of lateral boss 54, opposite an end including lateral notch 84, is positioned to substantially abut and be slidably received along medial-most wall surface 45B of lateral condyle wall 44. In this position, the end of medial boss 50 including medial notch 80 clears and is insertable past medial protrusion 82 of medial condyle wall 38, and the end of lateral boss 54 including lateral notch 84 clears and is insertable past lateral protrusion 86 of lateral condyle wall 44.

Once proximal ends of medial boss 50 and lateral boss 54 clear respective medial protrusion 82 of medial condyle wall 38 and lateral protrusion 86 of lateral condyle wall 44, removal of actuating force 60 allows for both a frictional engagement and a cooperating engagement between the respective bosses and condyle walls. Referring to FIG. 6, actuating force 60 (FIG. 5) can be removed so that biasing force 62 biases medial boss 50 into frictional engagement with medial condyle wall 38 and lateral boss 54 into frictional engagement with lateral condyle wall 44 in femoral provisional component 28, for example, and medial notch 80 mates into cooperative engagement with medial protrusion 82 of medial condyle wall 38 and lateral notch 84 mates into cooperative engagement with lateral protrusion 86 of lateral wall 44. FIG. 6 shows medial notch 80 moving exteriorly to mate with medial protrusion 82 and lateral notch 84 moving exteriorly, away from medial notch 80, to mate with lateral protrusion 86. In another embodiment, the medial notch may move interiorly to mate with an interior medial protrusion and the lateral notch may move interiorly, towards the medial notch, to mate with an interior lateral protrusion.

Figure 2:
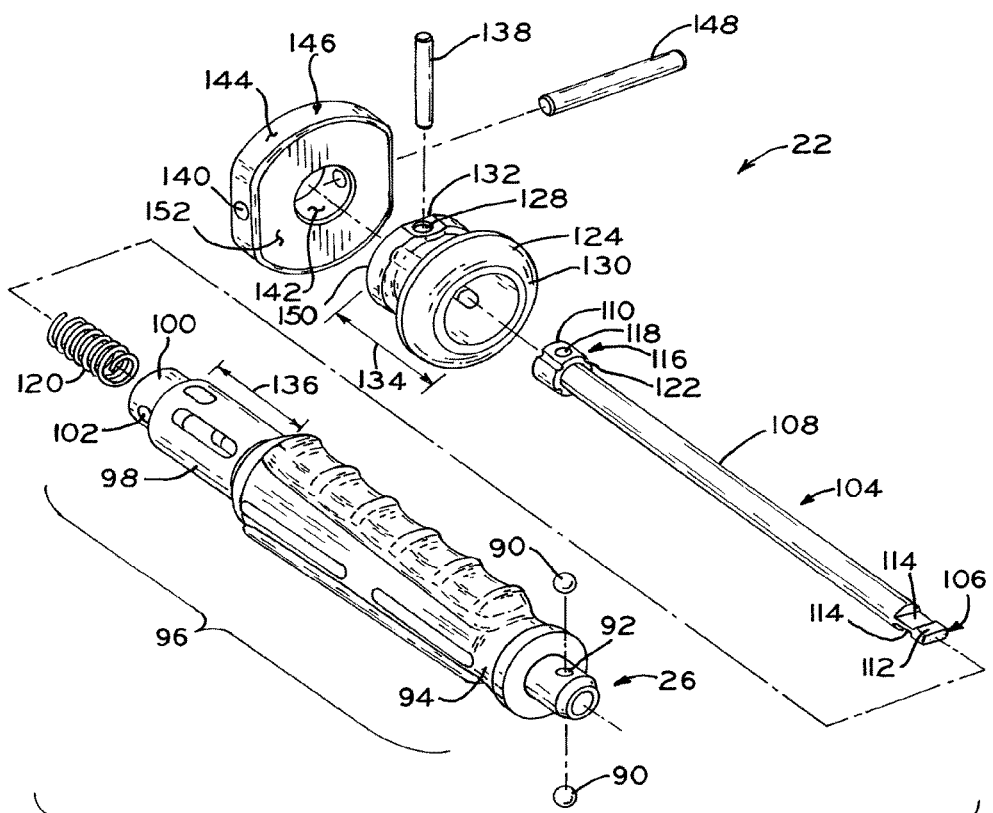
FIG. 2 is an exploded perspective view of an embodiment of a handle of the inserter assembly of FIG. 1.

Referring back to FIGS. 2 and 3, stationary body 64 (FIG. 3) includes at least a pair of inserter head holes 88, any one pair having holes 88 positioned across from one another to be capable of receiving retractable ball bearings 90 of handle 22 (FIG. 2). As shown in FIG. 2, ball bearings 90 are disposed within a pair of proximal holes 92 on proximal grip shaft 98 of elongate handle body 96, which also includes actuator shaft 98 positioned below grip shaft 94 and base shaft 100 positioned below actuator shaft 98. Base shaft 100 includes a pair of base shaft holes 102. Each of the ball bearings 90 includes in cross-section a diameter that is larger than the greatest diameters of the pair of proximal holes 92 so that ball bearings 90 will not completely pass through proximal holes 92.

Elongate ball retractor element 104 is disposed within handle body 96 and includes proximal end 106, intermediate body portion 108, and distal end 110. Proximal end 106 is proximally positioned with respect to femur 36 and distal end 110 is distally positioned with respect to femur 36, such that distal end 110 is positioned at a distance further away from femur 36 than proximal end 106. A pair of protrusions 112 distally extends from proximal end 106 and a pair of notches 114 extends from protrusions 112. Intermediate body portion 108 extends distally from notches 114, and distal base portion 116 is positioned between intermediate body portion 108 and distal end 110. Distal base portion 116 includes a pair of distal base portion holes 118. A biasing member such as spring 120 is positioned above and upon shoulder 122 of distal base portion 116 and along intermediate body portion 108. At an end opposite the end positioned upon shoulder 122, spring 120 is positioned against an internal shoulder (not shown) within actuator shaft 98.

Ball bearings 90 are retractable via actuator slide piece 124, which is positioned above base 146 along actuator shaft 98 and which includes a pair of actuator slide holes 128. Actuator slide piece 124 includes proximal end 130 and distal end 132 and actuator slide distance 134 is defined between ends 130 and 132. Actuator shaft distance 136 is defined between a proximal portion of actuator shaft 98 and a distal portion of actuator shaft 98. Actuator slide distance 134 is less than actuator shaft distance 136, allowing actuator slide piece 124 to slide along actuator shaft 98. Actuator slide holes 128 are aligned with distal base portion holes 118 of ball retractor element 104 to connect actuator slide piece 124 and ball retractor element 104 via pin 138, which is received through holes 128 and 118. Similarly, base shaft holes 102 are aligned with a pair of base holes 140 each extending through inner periphery 142 and outer periphery 144 of base 146 to connect base 146 and handle body 96 via pin 148 that is received through both holes 140 and 102.

In a locked position, ball bearings 90 are extended partially through the pair of proximal holes 92 and disposed against protrusions 112 of ball retractor element 104 (FIG. 6), and distal surface 150 of actuator slide piece 124 is positioned to abut proximal surface 152 of base 146 (FIG. 4). In an unlocked positioned (FIG. 5), ball bearings 90 are retracted from the pair of proximal holes 92 and disposed within notches 114 of ball refractor element 104, and distal surface 150 of actuator slide piece 124 is spaced from proximal surface 152 of base 146. In the unlocked position resulting from application of an actuating force upon actuator slide piece 124 in a proximal direction along arrow 154 (FIG. 5) that is parallel to axis 156 of handle 22, proximal end 26 of handle 22 may be inserted into a distal end of inserter head 24 via a boss and bore mating junction such that ball bearings 90 are retracted and the pair of proximal holes 92 are aligned with a pair of inserter head holes 88. When actuator slide piece 124 is released from the actuating force to return actuator slide piece 124 back to the locked position, ball bearings 90 extend through both the pair of proximal holes 92 and the pair of inserter head holes 88 to connect handle 22 to inserter head 24.

Figure 11:
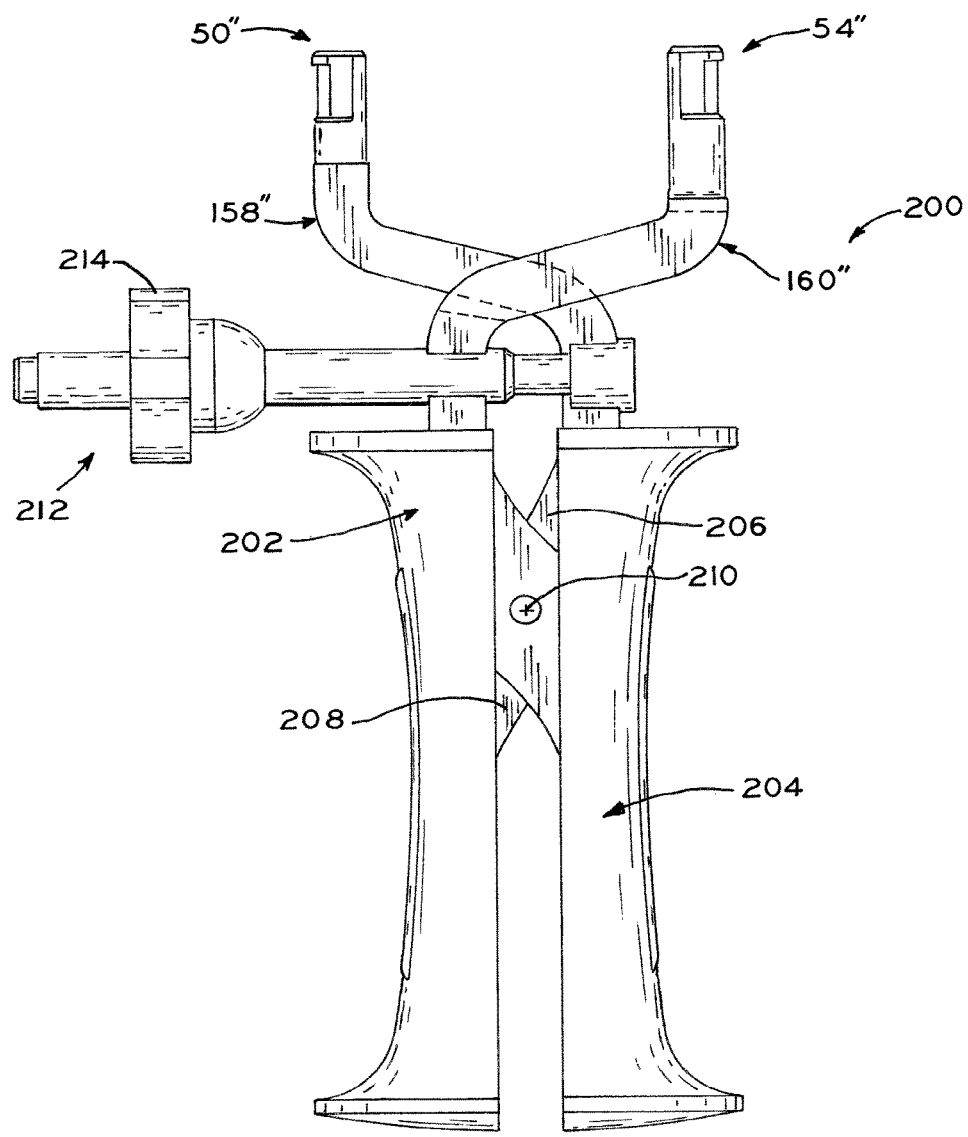
FIG. 11 is a top plan view of another embodiment of an inserter according to the present invention.
Figure 12:
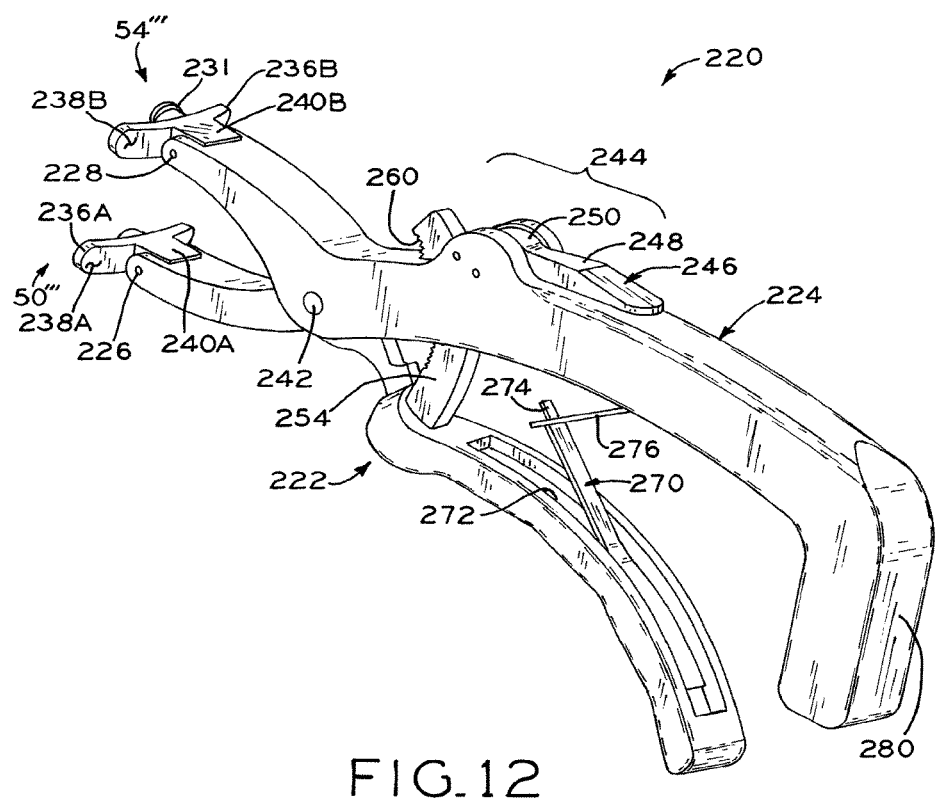
FIG. 12 is a perspective view of yet another embodiment of an inserter according to the present invention.
Figure 13:
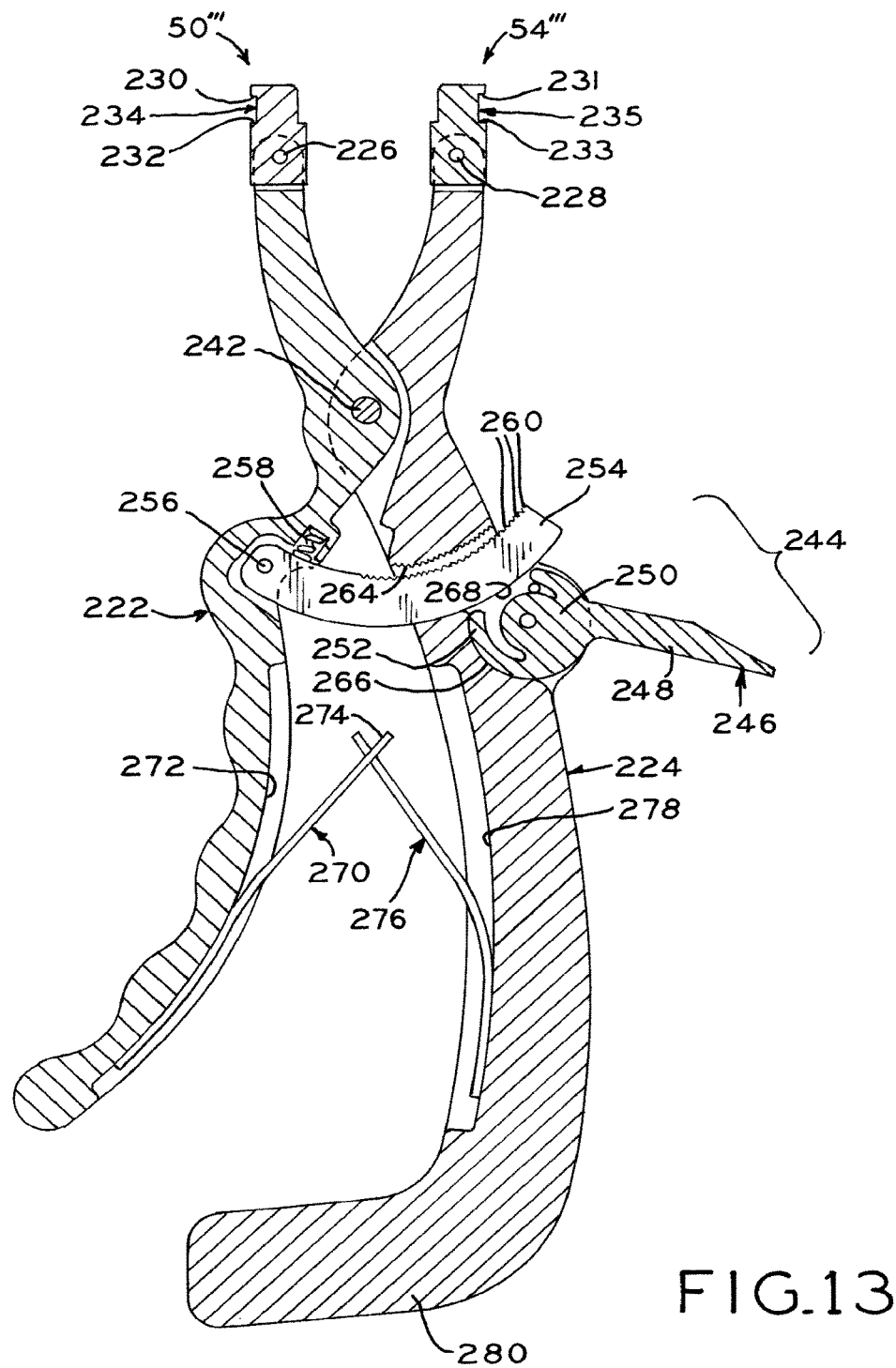
FIG. 13 is a cross sectional view of the inserter of FIG. 12 in an open position.
Figure 14:
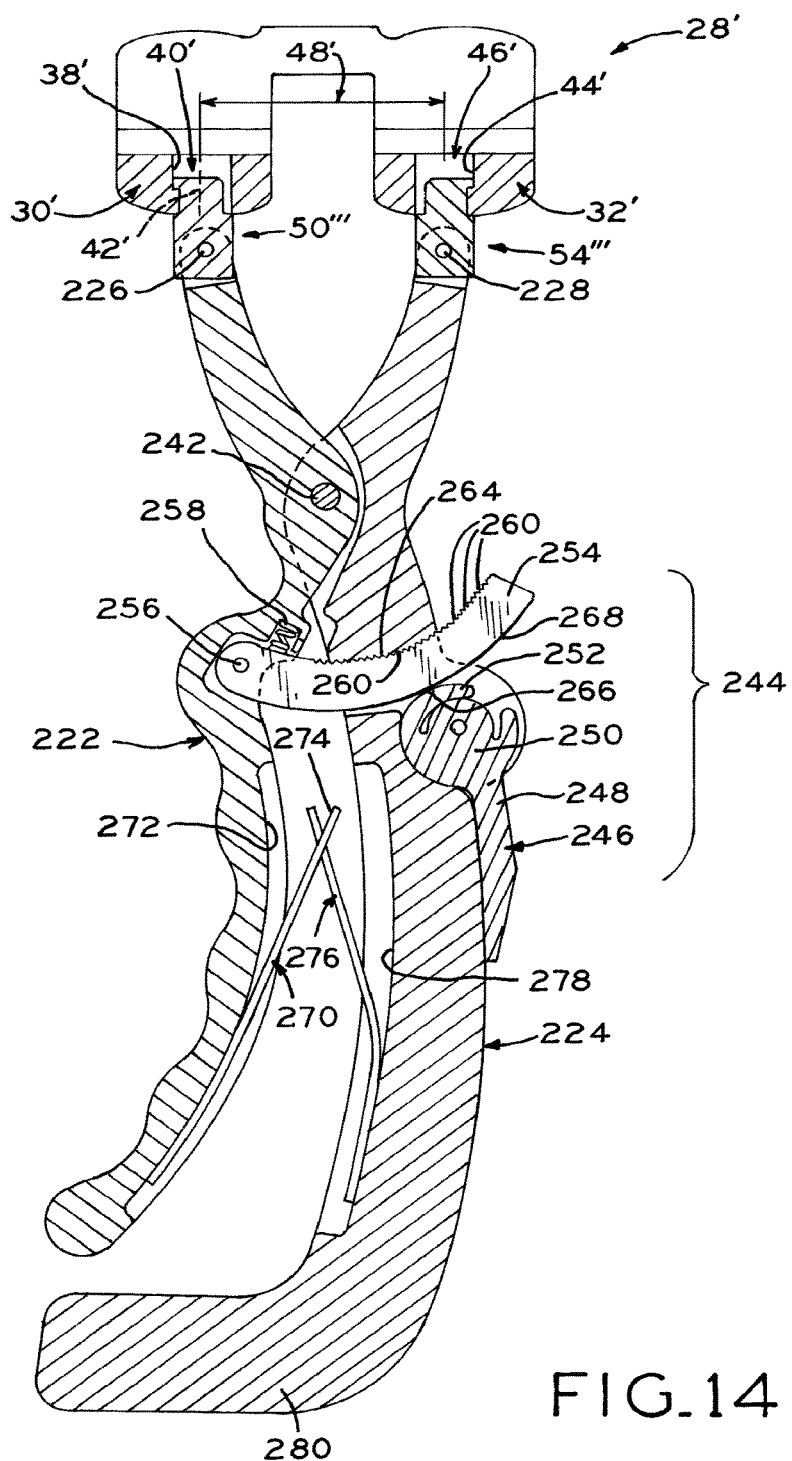
FIG. 14 is a cross-sectional view of the inserter of FIG. 12 in a closed position in which bosses of the inserter are shown to matingly engage with a pair of condyle apertures in a femoral provisional component.

According to other embodiments, an inserter includes a multi-bar handle that directly connects to a medial boss and a lateral boss similar to medial boss 50 and lateral boss 54 of the above described embodiment via one or more of the bars of the handle. For example, one such embodiment is shown in FIGS. 7-10, another is shown in FIG. 11, and yet another is shown in FIGS. 12-14. The medial and lateral bosses of each of these embodiments matingly engage with respective condyle aperture walls of a femoral provisional component via respective mating shoulder arrangements also similar to those described in the embodiment above. However, while application of an actuating force in the above embodiment causes an inwards movement of one of medial boss 50 and lateral boss 54, an actuating force in the below embodiments will cause the medial and lateral bosses to both move away from one another.

The embodiment of FIGS. 7-10 shows inserter 156 as including medial boss 50' and lateral boss 54' each integrally connected to S-shaped bars 158 and 160 including intermediate portions 162 and 164, respectively. Intermediate portions 162 and 164 of S-shaped bars 158 and 160, respectively, cross each other, and a distal end of each S-shaped bar is positioned along an axis parallel but not coincident to a boss axis of the boss to which the S-shaped bar is connected. Referring to FIG. 7, S-shaped bar 158 is connected at distal end 170 to impactor bar 166 and S-shaped bar 160 is connected at distal end 172 to grip bar 168. Alternatively, distal end 170 of S-shaped bar 158 may be connected to grip bar 168 and distal end 172 of S-shaped bar 160 may be connected to impactor bar 166.

Figure 8:
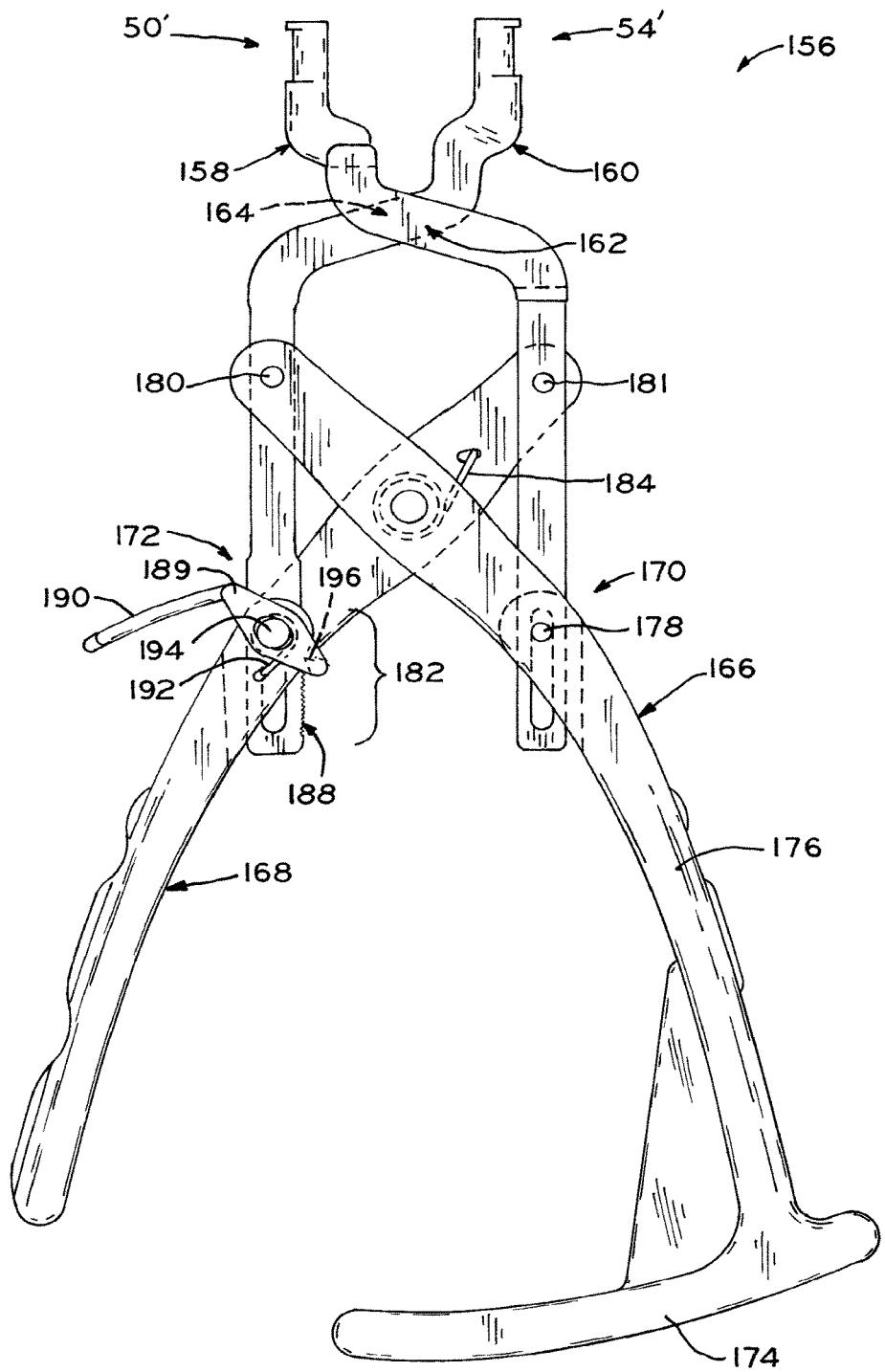
FIG. 8 is a top plan view of the inserter of FIG. 7 in an open position.
Figure 9:
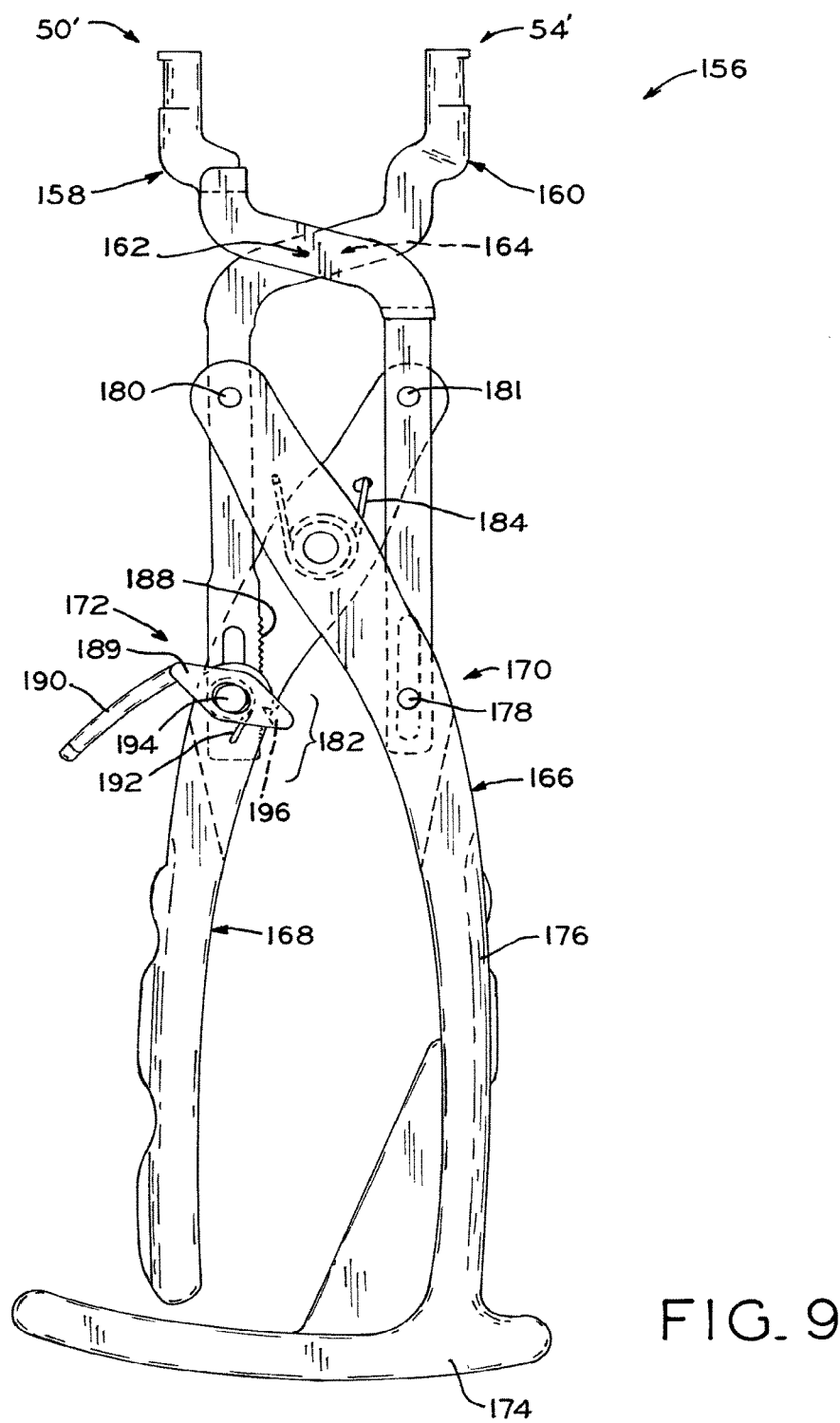
FIG. 9 is a top plan view of the inserter of FIG. 7 in a closed position.

Impactor bar 166 includes impactor 174 and grip portion 176 extending from impactor 174, which may receive impaction force from a surgical tool such as, for example, a hammer. The connection of distal end 170 of S-shaped bar 158 to impactor bar 166 occurs, for example, via pin 178. An intermediate portion of the S-shaped bar 160 is connected to impactor bar 166 via pin 180 (FIG. 8). S-shaped bar 160 further has distal end 172 connected to grip bar 168 via ratchet mechanism 182, and an intermediate portion of S-shaped bar 160 is connected to grip bar 168 via pin 181 (FIG. 8). Impactor bar 166 and grip bar 168 cross in an area disposed between distal ends 170 and 172 of S-shaped bars 158 and 160, respectively, and are further connected via spring coil 184. Grip bar 168 and grip portion 176 of impactor bar 166 may be gripped to position inserter 156 into an actuated or closed position (FIG. 9) in which distal ends of grip bar and 168 impactor bar 166 are actuated towards one another, simultaneously moving medial boss 50' and lateral boss 54' away from one another to be spaced at a closed position boss distance that is greater than an open position boss distance in which distal ends of impactor bar 166 and grip bar 168 are positioned at a greatest distance away from one another (FIG. 8). Distal ends of impactor bar 166 and grip bar 168 can be held in place by ratchet mechanism 182.

Figure 10:
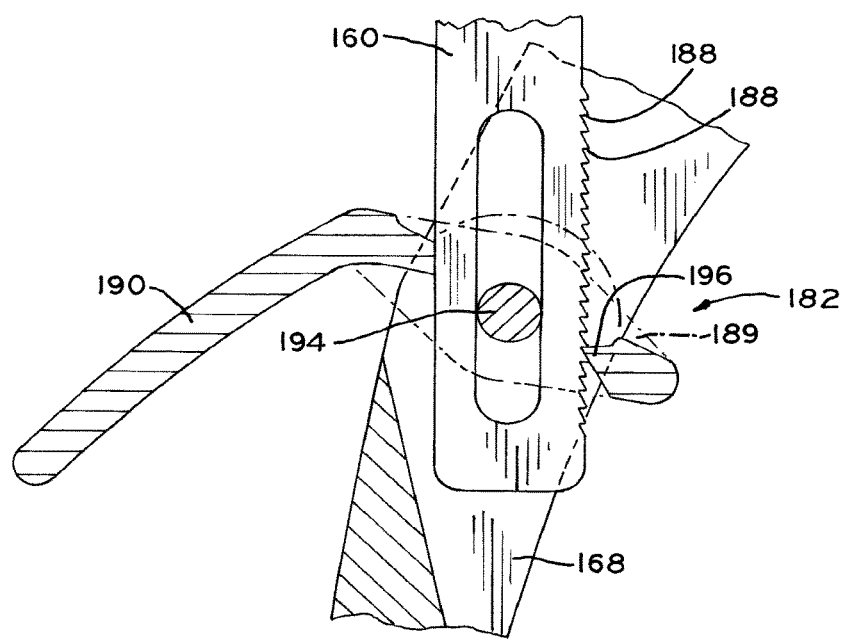
FIG. 10 is a fragmentary cross-sectional view of a ratchet used to maintain the position of the inserter of FIG. 7.

Referring to FIG. 10, ratchet mechanism 182 includes movable pawl 196 and a series of ratchet teeth 188 on a distal end of S-shaped bar 160, each tooth engageable by pawl 196. Movable pawl 196 includes body 189 and handle 190. Body 189 abuts grip bar 168 and includes an aperture receiving pin 194 to rotationally couple, via spring 192, body 189 to grip bar 168 and S-shaped bar 160. Handle 190 extends from body 189 at a first end and is spaced away from an outer gripping surface of grip bar 168. Pawl 196 extends from body 189 at a second end opposite the first end and is disposed in a space between grip bar 168 and impactor bar 166.

Pawl 196 includes wall surfaces defining an oblique angle that corresponds to angles of multiple, identical ratchet teeth 188 in the distal end of the S-shaped bar, which are obliquely angled with respect to a longitudinal axis of the distal end of the S-shaped bar. Via the mirroring oblique angles, movable pawl 196 mates with a selected tooth 188 when a biasing force is applied via spring 192, with handle 190 at rest, such that impactor bar 166 and grip bar 168 cannot move apart from one another. When a force is applied upon handle 190 inwards towards grip bar 168, grip bar 168 and impactor bar 166 are unlocked from a locked position via removal of a biasing force from spring 192 and are movable away or towards one another. The applied force upon handle 190 causes a distal end of movable pawl 196 to be spaced a distance away from proximal ends of wall surfaces defining teeth 188. Releasing the applied force from handle 190 causes pawl 196 to mate with one of teeth 118, locking grip bar 168 and impactor bar 166 into a desired, locked position.

Even in the locked position, an application of a force upon each of impactor bar 166 and grip bar 168 may move impactor bar 166 and grip bar 168 towards each other, though impactor bar 166 and grip bar 166 cannot be moved away from one another without application of the actuating force on handle 190 to remove the biasing force applied by spring 192. The force applied upon the impactor bar 166 and grip bar 168 causes the distal end of pawl 196 to slide up a first ramped wall surface defining one of teeth 118 in which pawl 196 was received until pawl 196 slides over the proximal part of the first ramped wall surface onto a second ramped wall surface defining a second one of teeth 118 into which pawl 196 is next received.

Referring to FIG. 11, showing another embodiment, inserter 200 includes similar S-shaped bars 158" and 160", also connected at proximal ends to medial boss 50" and lateral boss 54". Bars 158" and 160" connect at distal ends to grip bars 202 and 204, respectively. Grip bars 202 and 204 are connected to one another via cross bars 206 and 208, which are attached at pivot 210, for example. Screw mechanism 212 includes a threaded screw assembly in which nut 214 is rotatable in one direction to move grip bars 202 and 204 towards one another, allowing medial boss 50" and lateral boss 54" to be spaced at a farther distance away from one another than when the grip bars 202 and 204 are positioned away from another by rotating nut 214 in the opposite direction.

Referring to FIGS. 12-14, in yet another embodiment, inserter 220 includes medial boss 50''' and lateral boss 54''' that are connected to medial handle 222 and lateral handle 224, respectively, via medial pin 226 and lateral pin 228, respectively. Referring to FIG. 13, medial and lateral bosses 50''' and 54''' each respectively include proximal shoulder 230, 231 and distal shoulder 232, 233 with notch 234, 235 defined in between the proximal and distal shoulders. Any of the bosses of the present disclosure may include such a double shoulder structure defining a notch therebetween. Respectively extending distally from each distal shoulder 232, 233 is distal curved portion 236A and 236B. Distal surface 238A, 238B of distal curved portion 236A, 236B, respectively, is seated above a proximal surface of each respective handle 222 and 224. Extending from either side of distal curved portion 236A, 236B are extensions 240A, 240B, respectively, which are each respectively positioned in grooves formed between proximal ends of handles 222 and 224 such that an aperture in each flange aligns with a pair of holes in the proximal ends of the handles. Pins 226 and 228 may then be received through the respective apertures and holes along the alignment path. Bosses 50''' and 54''' are rotatable about pins 226 and 228, respectively.

Further, lateral handle 224 is pivotally connected at a proximal intermediate portion to a proximal intermediate portion of medial handle 222 via pin 242. Medial handle 222 is rotatable about pin 242 via ratchet mechanism 244 such that a distal portion of medial handle 222 disposed distal to pin 242 is movable towards or away from a corresponding distal portion of lateral handle 224. When the distal portion of medial handle 222 moves towards lateral handle 224, medial boss 50''' moves further away from lateral boss 54''', and when the distal portion of medial handle 222 moves away from lateral handle 224, medial boss 50''' moves towards lateral boss 54'''.

As described above, such movement occurs via cam mechanism 244, which includes handle 246. Handle 246 includes shaft 248 and arcuate head 250, which has cam 252. Cam mechanism 244 further includes curved rack 254 pinned at a medial end to medial handle 222 via pin 256, the medial end subject to a biasing force via spring 258 disposed in medial handle 222. Rack 254 extends at the other lateral end through an aperture of lateral handle 224 and past an outer peripheral surface of lateral handle 224. The aperture extends from an internal peripheral surface to an external peripheral surface of lateral handle 224. Along a proximal surface, rack 254 includes a series of adjacently positioned teeth 260 that are sized to intermesh with a series of opposing teeth 264 disposed along a proximal internal wall defining the aperture of lateral handle 224.

In an open and unlocked position (FIG. 13), proximal surface 266 of cam 252 is spaced from distal surface 268 of rack 254 so that a gap is created between teeth 260 of rack 254 and teeth 264 of handle 224 to allow for movement between handles 222 and 224. In a closed and locked positioned (FIG. 14), cam mechanism 244 is subject to a force placed upon handle 246 such that, when cam mechanism 244 is released from the force, proximal surface 266 of cam 252 abuts distal surface 268 of rack 254 so that a gap does not remain between teeth 264 of handle 224 and teeth 260 of rack 254, as the teeth intermesh with one another. Upon return of handle 246 to the position illustrated in FIG. 13, the biasing force of spring 258 assists to disengage cam 252 from rack 254.

Distal medial elongate piece 270 is positioned within distal notch 272 of medial handle 222 disposed below curved piece 254 and includes proximal tab portion 274 received within a notch defined by a pair of flanges (not shown) extending from a proximal end of distal lateral elongate piece 276 similarly positioned within, for example, distal notch 278 of lateral handle 224 (FIGS. 13 and 14). Distal medial resilient extension 270 and distal lateral resilient extension 276 provide an outwards biasing force against each other and the walls defining the distal notches of the medial and lateral handles such that, when an actuation force is applied on the inserter, the actuation force acts against the biasing force of resilient extensions 270 and 276. In an embodiment, inserter 220 includes impactor 280 on a distal end of lateral handle 224 for receipt of an impaction force transmitted via impaction by a surgical tool, such as a hammer.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A handle for releasable securement to a surgical tool, comprising:
   a handle body, including a proximal end configured to be secured to a surgical tool;
   a detent ball disposed within the handle body, adjacent the proximal end;
   a retractor, moveable in relation to the handle body to selectively position the detent ball between a release position and a locking position; and
   an actuator surrounding the handle body and fixedly engaged with the retractor.

2. The handle of claim 1, wherein the actuator is slidable over a portion of the handle body.

3. The handle of claim 1, further comprising a base connected to the handle body opposite the proximal end.

4. The handle of claim 3, wherein the actuator is disposed between the proximal end and the base.

5. The handle of claim 1, wherein the handle body further comprises a grip shaft disposed above the actuator.

6. The handle of claim 5, wherein the actuator is disposed to abut the base when the retractor is in the locking position.

7. The handle of claim 1, wherein the actuator comprises an actuator bore and the retractor comprises a retractor bore, the actuator engaged with the retractor through a pin received in the actuator bore and the retractor bore.

8. The handle of claim 1, wherein the handle body further comprises a base shaft disposed below the actuator.

9. The handle of claim 3, wherein the base comprises a base bore, and wherein the handle body comprises a body bore, the base engaged with the handle body through a pin received within the base bore and the body bore.

10. The handle of claim 1, wherein the retractor comprises a shoulder configured for engagement with the actuator.

11. The handle of claim 10, further comprising a biasing member configured to bias the retractor to position the detent ball in the locking position, the biasing member disposed on the shoulder of the retractor.

12. A system, comprising:
a handle for releasable securement to a surgical tool, comprising:
a shaft having a proximal end;
a pair of detent balls, disposed adjacent the shaft proximal end;
a retractor, configured to selectively move the pair of detent balls between a retracted position and an extended position; and
a prosthetic component inserter head, including a pair of detent features, configured to be coupled to the handle through locking engagement of the pair of detent balls and the pair of detent features.

13. The system of claim 12, the handle further comprising an actuator configured to move the retractor relative to the shaft.

14. The system of claim 12, the handle further comprising a base and an actuator, wherein the actuator is disposed to abut the base when the pair of detent balls is in the extended position, and wherein the actuator is spaced from the base when the pair of detent balls is in the retracted position.

15. A surgical tool system, comprising:
a handle for releasable securement to a surgical tool, comprising:
a shaft, including a pair of bores disposed adjacent a shaft proximal end;
a pair of detent balls, disposed within the shaft;
a base;
an actuator disposed between the shaft proximal end and the base, the actuator configured to move the retractor relative to the shaft; and
a retractor, movable relative to the shaft, the retractor configured to selectively position the pair of detent balls in a retracted position or in an extended position; and
a surgical tool, configured to be coupled to the shaft proximal end, including a pair of detent features configured to receive the pair of detent balls.

16. The system of claim 15, the handle further comprising a biasing member configured to bias the retractor to position the pair of detent balls in the extended position.

17. The system of claim 15, wherein each one of the pair of detent balls is configured to partially extend through a respective one of the pair of bores when the pair of detent balls is in the extended position.

18. The system of claim 15, wherein the actuator abuts the base when the pair of detent balls is in the extended position and the actuator is spaced from the base when the pair of detent balls is in the retracted position.

19. The system of claim 13, wherein the actuator surrounds the shaft.

20. The system of claim 12, wherein the prosthetic component inserter head comprises a pair of bosses configured for engagement with a prosthesis.

* * * * *